United States Patent [19]
Parker et al.

[11] Patent Number: 5,425,815
[45] Date of Patent: Jun. 20, 1995

[54] CLEANING AND DISINFECTING ENDOSCOPIC MEDICAL INSTRUMENTS

[75] Inventors: George C. Parker, Westcliffe-on-Sea; Ian M. Ross, Leigh-on-Sea, both of United Kingdom

[73] Assignee: Keymed (Medical & Industrial Equipment) Limited, Southend on Sea, United Kingdom

[21] Appl. No.: 30,082
[22] PCT Filed: Sep. 20, 1991
[86] PCT No.: PCT/GB91/01615
  § 371 Date: Apr. 14, 1993
  § 102(e) Date: Apr. 14, 1993
[87] PCT Pub. No.: WO92/04858
  PCT Pub. Date: Apr. 2, 1992

[30] Foreign Application Priority Data

Sep. 20, 1990 [GB] United Kingdom ............. 9020559.2

[51] Int. Cl.[6] .................... B08B 3/04; B08B 3/02; A61L 2/18; A61L 2/24
[52] U.S. Cl. ........................................ 134/26; 134/2; 134/22.11; 134/29; 134/42; 422/28
[58] Field of Search ............. 134/2, 22.11, 22.14, 134/34, 36, 42, 26, 29; 422/28, 37

[56] References Cited

U.S. PATENT DOCUMENTS

4,281,674  8/1981  Tanaka et al. .................... 134/95
4,784,790  11/1988  Disch et al. .................... 252/174.12

FOREIGN PATENT DOCUMENTS

0072257  2/1983  European Pat. Off. .
2947576  6/1980  Germany .
3334999  4/1985  Germany .

*Primary Examiner*—Paul Lieberman
*Assistant Examiner*—Lorna M. Douyon
*Attorney, Agent, or Firm*—Kenyon & Kenyon

[57] ABSTRACT

A method of cleaning medical instruments comprises the steps of placing an instrument in an enclosure and subjecting the instrument to a cleaning phase in which a cleansing solution is applied to the surfaces of the instrument, a disinfection phase in which a disinfection solution is applied to the surfaces of the instrument, a rinsing phase in which a flushing solution is applied to the surfaces of the instrument, a purging phase in which a volatile liquid is applied to the surfaces of the instrument and a drying phase in which a drying gas is passed over the surfaces of the instrument. The method is particularly suited for use with endoscopes.

8 Claims, 1 Drawing Sheet

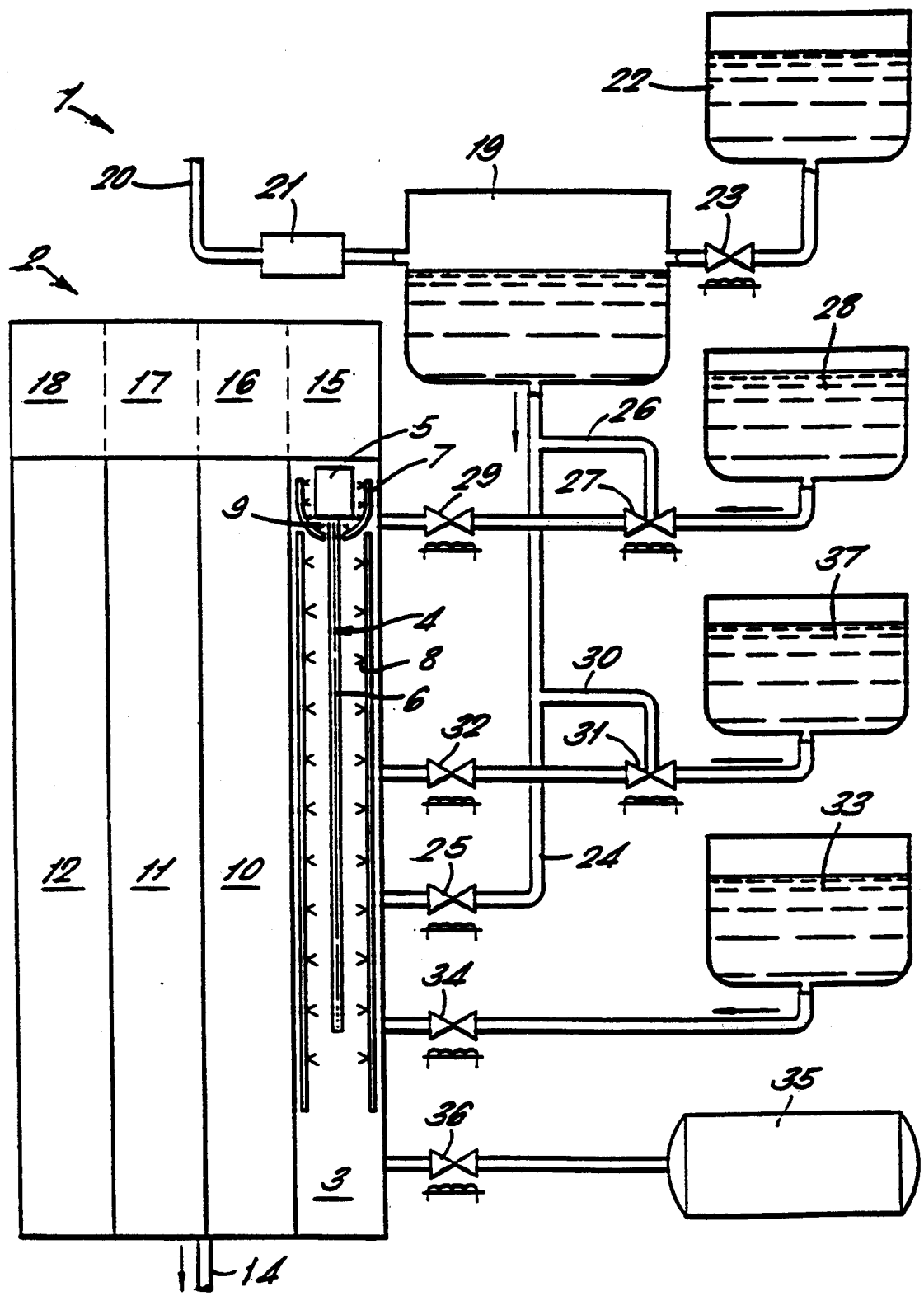

CLEANING AND DISINFECTING ENDOSCOPIC MEDICAL INSTRUMENTS

This invention relates to cleaning and disinfecting medical instruments and in particular but not exclusively to cleaning and disinfecting medical endoscopes.

Particular care is necessary in the cleaning and disinefection of medical instruments such as flexible endoscopes which although immersible in aqueous solution cannot be heated to the temperatures normally associated with sterilizing equipment. In particular there are difficulties in ensuring the endoscopes are thoroughly cleaned and disinfected after each use since they tend to be heavily contaminated in use both externally and internally in the narrow channels which typically extend longitudinally through a flexible insertion tube of a flexible endoscope, The present invention seeks to provide improvements in the apparatus and method used in such cleansing and disinfection of instruments including flexible endoscopes.

According to the present invention a method of cleaning medical instruments comprises the steps of placing the instrument in an enclosure and subjecting the instrument to a cleaning phase in which a cleansing solution is applied to the surfaces of the instrument, a disinfection phase in which a disinfecting solution is applied to the surfaces of the instrument, a rinsing phase in which a flushing solution is applied to the surfaces of the instrument, a purging phase in which a volatile liquid is applied to the surfaces of the instrument and a drying phase in which a drying gas is passed over he surfaces of the instrument.

Preferably the volatile livid is alcohol and the drying gas is sterile compressed air.

An advance of such a method is that any microbes or bacteria remaining on the surfaces of the instrument after the further rinsing phase will be destroyed and removed by the alcohol. Since alcohol is highly volatile the drying phase then leaves the instrument thoroughly dried. Removal of moisture from the instrument reduces the likelihood of colonisation by opportunistic organisms.

This use of alcohol also enables the instrument to decontaminated without reliance on more powerful disinfectants such as formaldehyde or glutaraldehyde, the vapours from which are known to cause adverse reactions in a significant proportion of hospital staff. The disinfectant used in the disinfection phase may then be a less powerful disinfectant such as quaternary ammonium compound.

Preferably the cleaning phase is followed by a further rinsing phase in which a flushing solution is applied to the surfaces of the instrument.

The instrument may be an endoscope having a handpiece which is supported in a cradle within the enclosure such that the endoscope depends from the cradle. The cradle may be provided with upwardly directed jet nozzles whereby during the cleaning, rinsing, disinfection and purging phases the handpiece is lifted clear of contact with the cradle by liquid pressure from liquid emerging from the jet nozzles. All surfaces of the instrument are then accessible for cleaning.

Preferably fluid applied to the endoscope surfaces during each phase is removed from the enclosure via a waste outlet without being re-circulated into further contact with the endoscope surfaces.

Preferably the rinsing solution includes a disinfectant whereby pipe work leading to the enclosure may be automatically disinfected in use.

Preferably the cleaning, rinsing, disinfection and volatile liquids which are required for the cleaning, rinsing, disinfection and purging phases respectively are held in closed containers. The closed containers are preferably connected to the enclosure via control valves operable under the control of a programme controller.

Conveniently a plurality of instruments are cleaned in a plurality of like enclosures each operable to accommodate one or more instruments in use and each enclosure being associated with a respective programme controller whereby cleaning and disinfecting sequence is performed in the respective enclosures under the independent control of the respective programme controllers.

In accordance with the present invention there is also disclosed apparatus for use in the above method of cleaning medical instruments comprising at least one enclosure ad respective containers receiving fluids for use in cleaning, rinsing, disinfection and purging phases, the containers being connected to the enclosure via respective control valves operable under the control of a programme controller.

An embodiment of the resent invention will now be described by way of example only and with reference to the accompanying drawing in which FIG. 1 is a schematic elevation of cleaning and disinfection apparatus containing a flexible endoscope.

In Figure 1 a cleaning and disinfecting apparatus 1 consists of a washing machine 2 having a first enclosure 3 in which a flexible endoscope 4 is received. The endoscope 4 has a handpiece 5 containing optical elements and control devices (not shown) and a flexible insertion tube 6 housing a fibre optic light guide and narrow bore channels for the performance of various procedures.

The handpiece 5 is supported in a cradle 7 with the insertion tube 6 depending through the cradle within the first enclosure 3o The cradle 7 and the side walls of the first enclosure 3 are provided with jet nozzles 8 through which liquid may be sprayed under pressure onto the external surfaces of the handpiece 5 and the insertion tube 6. The cradle 7 includes a number of upwardly directed jet nozzles 9 arranged to deliver an upward force on the handpiece 5 by means of pressurised liquid delivered from the jet nozzles.

Second, third and fourth enclosures 10, 11 and 12 respectively are also included in the washing machine 2 and are similarly constructed to the first enclosure 3 and similarly receive further endoscopes (not shown).

The enclosures 3, 10, 11 and 12 are provided with an outlet 14 for the drainage of waste fluids.

The enclosures 3, 10, 11 and 12 are provided respectively with programme controllers, 15, 16, 17 and 18 each including an electronic processor controlling the functions of the washing machine 2 in a programmable manner.

The apparatus 1 is further provided with a cold water storage tank 19 supplied with water through an inlet pipe 20 in-line with a bacterial filter 21. A container of concentrated disinfectant 22 is connected to the cold water storage tank 19 via a control valve 23.

A first outlet pipe 24 connects the cold water 35 storage tank 19 with the first enclosure 3 via a control valve 25 and the washing machine 2 includes a pump (not shown) for pressurising water received through the first outlet pipe to be delivered via the jet nozzles 8 and 9 onto the external surfaces of the endoscope 4. The enclosure 3 is also provided with connectors (not shown) which supply fluid to one end of each endoscope channel.

A second outlet pipe 26 connects the cold water storage tank 19 to a mixer valve 27 connected to a container of detergent 28 whereby water mixed with detergent may be conducted to the first enclosure 3 via a control valve 29.

A third outlet pipe 30 connects the cold water storage tank 19 with a second mixer valve 31 which is connected to a container of liquid disinfectant 37 such that disinfectant mixed with water may be delivered to the first enclosure 3 from the second mixer valve via a control valve 32.

A container of alcohol 33 is also connected to the first enclosure 3 via a control valve 34 and a supply of sterile compressed air 35 is connected to the first enclosure 3 via a control valve 36..

Each of the control valves 29, 32, 25, 34 and 36 are selectively operable under the control of the programme controller 15 to admit respective fluids to the jet nozzles 8 and 9 and the connectors communicating with the channels of the endoscope 4.

The second, third and fourth enclosures 10, 11 and 12 respectively are provided with corresponding pipe work and control valves (not shown) and similarly can accomodate flexible endoscopes supported in a cradle with jet nozzles and connectors coupled to the internal channels of the endoscope. The respective endoscopes within the enclosures 3, 10, 11 and 12 can be cleaned independently under independent control of the programme controllers 15, 16, 17 and 18 respectively.

In use an endoscope 4 within the first enclosure 3 is cleaned and disinfected in accordance with the following process. The soiled endoscope is first supported in the cradle 7 and the connectors fitted to the uppermost end of each of the internal channels of the endoscope.

A cleaning phase is then commenced in which water from the cold water storage tank 19 is mixed with detergent from the detergent container 28 in the mixer valve 27 and admitted to the enclosure 3 by operation of control valve 29. The mixed solution is pumped under pressure through the jet nozzles 8 and 9 and through the endoscope channels for a period sufficient to thoroughly clean the endoscope both externally and internally.

A rinsing phase then follows in which water from the cold water storage tank 19 is mixed with a small quantity of disinfectant from the disinfectant container 22 by operation of valve 23 and flows into the enclosure 23 via control valve 25. The endoscope is cleaned with this rinsing solution for a period of time sufficient to flush the residual detergent from the endoscope.

A disinfection phase then follows in which disinfectant from the disinfectant container 37 is mixed with water from the cold water storage tank 19 in the mixing valve 31 and delivered to the enclosure 3 via control valve 32. The resulting disinfecting solution is pumped under pressure to be sprayed onto the external surfaces of the endoscope and is also passed through the internal channels of the endoscope for a period of time sufficient to complete disinfection of the endoscope.

A further rinsing phase then follows using the steps described above with reference to the first rinsing phase.

A purging phase then follows in which all aqueous solutions are purged from the endoscope 4 by means of alcohol delivered from the alcohol container 33 to the enclosure 3 via control valve 36. Alcohol is sprayed onto the endoscope and also passed through the endoscope channels for a period of time sufficient to remove all traces of aqueous solution from the internal and external surfaces of the endoscope. The alcohol remaining at the end of this purging phase is then vaporised and dispersed from the enclosure 3 by a final drying phase in which sterile compressed air is admitted to the enclosure via control valve 36 and is blown onto the external surfaces and through the channels of the endoscope for a period of time sufficient to remove all traces of alcohol in liquid and vapour form.

The endoscope is then in a cleansed and disinfected condition ready for re-use.

The second, third and fourth enclosures 10, 11 and 12 may similarly contain further endoscopes and be operated under the programme controllers 16, 17 and 18 using corresponding sequences which may commence in unison or at separate times. Where different types of endoscopes are being cleaned in the respective enclosures it may be necessary to vary the timing of the cleaning, flushing, disinfecting, purging and drying phases by the input of suitable commands to the programme controllers.

The disinfectant container 22 typically contains hyperchlorite which is added to the cold water storage tank 19 at a dosage rate of 100 to 125 parts per million. In the disinfection phase the disinfecting solution is a typically hyperchlorite solution of 500 parts per million. In the cleaning phase the detergent is typically an enzymatic detergent.

Each of the tanks 22, 28, 37, 33 and 19 may be a sealed container provided with means to allow air to enter the container as the liquid level drops. The escape of potentially hazardous vapours may be minimised by providing filters suitable for dealing with the specific vapours concerned. Such measures may be required to meet health and safety requirements for the operator concerned.

The tanks may in some instances be replaced by collapsible airtight containers.

An additional step of preparatory pre-cleaning may sometimes be required when using apparatus in accordance with the present invention and in particular it may be necessary to pre-clean the endoscope channels by flushing with water and, in the case of larger diameter channels, cleaning with a brush passed through the channels. Apparatus in accordance with the present invention may be modified to include automatic pre-cleaning within the enclosure for example by the automatic insertion of a brush through one or more channels of the endoscope. Pre-cleaning of endoscope channels may alternatively be accomplished by the insertion of a catheter delivering jets of water along the length of a channel or alternatively by the use of pulsed, turbulent or vortical flow of liquid through the channels to promote agitation and cleaning. The catheter may alternatively be provided with an ultrasonic transducer which is excitable to aid cleaning.

A pre-cleaning phase may alternatively include the use of heated detergent for example using a temperature of between 50° and 60° C.

We claim

1. A method of cleaning endoscopic medical instruments comprising the steps of;
    a) placing an instrument in an enclosure and subjecting said instrument to a cleaning phase in which a detergent cleansing solution is applied to the external surfaces of said instrument and to the internal surfaces of said instrument by being passed through internal channels of said instrument, b) followed by subjecting said instrument to a disinfection phase in which a disinfecting solution is applied to said external surfaces and to said internal surfaces by being passed through said internal channels, c) followed by subjecting said instrument to a rinsing phase in which a flushing solution is applied to said external surfaces of said instrument and to said internal surfaces of said instrument by being passed through said internal channels, d) subjecting said instrument to a drying phase in which a drying gas is passed over said external surfaces of said instrument and over said internal surfaces of said instrument by being passed through said internal channels, e) subjecting said instrument to a purging phase conducted after said rinsing phase (c) and before said drying phase (d) and in which liquid alcohol is applied to said external surfaces of said instrument and to said internal surfaces of said instrument by being passed through said internal channels whereby residual moisture following said rinsing phase (c) is removed from said surfaces prior to said drying phase (d) wherein fluid applied to the instrument surfaces during each phase is disposed of following removal from the enclosure via a waste outlet without being re-circulated into further contact with the instrument surfaces.

2. A method as claimed in claim 1 wherein the drying gas is compressed air.

3. A method as claimed in claim 1 in which the cleaning phase is followed by a further rinsing phase in which a flushing solution is applied to the surfaces of the instrument.

4. A method as claimed in claim 1 including the step of supporting the instrument in a cradle within the enclosure and directing fluid onto the instrument during at least one of the cleaning, rinsing, disinfection and purging phases via upwardly directed jet nozzles such that the instrument is lifted clear of contact with the cradle.

5. A method as claimed in claim 4 wherein the instrument is an endoscope having a handpiece connected to an insertion tube, the endoscope being supported in use such that the handpiece is supported by the cradle and the insertion tube depends therefrom.

6. A method as claimed in claim 1 wherein the rinsing solution is passed through a pipe leading to the enclosure, said rinsing solution including a disinfectant whereby said pipe is disinfected in use.

7. A method as claimed in claim 1 wherein the cleaning liquid, rinsing liquid, disinfection liquid and alcohol which are required for the cleaning, rinsing, disinfection and purging phases respectively are held in closed containers connected to the enclosure via control valves operable under the control of a program controller.

8. A method as claimed in claim 7 wherein a plurality of instruments are cleaned in a plurality of like enclosures each operable to accommodate one or more instruments in use and each enclosure being associated with a respective program controller whereby cleaning and disinfecting sequences is performed in the respective enclosures under the independent control of the respective program controllers.

* * * * *